США006797673B1

(12) United States Patent
Worthley et al.

(10) Patent No.: US 6,797,673 B1
(45) Date of Patent: Sep. 28, 2004

(54) LECITHIN-CONTAINING DRIFT REDUCTION COMPOSITION FOR USE IN SPRAYING AGRICULTURAL ACREAGE

(75) Inventors: Randall Worthley, Greeley, CO (US); Daniel Bergman, Greeley, CO (US)

(73) Assignee: Platte Chemical Company, Greeley, CO (US)

(*) Notice: Subject to any disclaimer, the term of this patent is extended or adjusted under 35 U.S.C. 154(b) by 0 days.

(21) Appl. No.: 10/322,963

(22) Filed: Dec. 18, 2002

Related U.S. Application Data
(60) Provisional application No. 60/377,468, filed on May 1, 2002.

(51) Int. Cl.[7] .......................... A01N 63/00; A01N 43/40
(52) U.S. Cl. ........................ 504/148; 504/118; 504/130; 504/173
(58) Field of Search ................................ 504/148, 173, 504/130, 118, 206, 362; 514/975

(56) References Cited

U.S. PATENT DOCUMENTS

| | | | |
|---|---|---|---|
| 3,682,653 A | | 8/1972 | Mommer et al. |
| 4,666,747 A | | 5/1987 | Quinn |
| 5,102,442 A | * | 4/1992 | Hazen et al. .................. 71/91 |
| 5,550,224 A | | 8/1996 | Hazen |
| 5,824,797 A | | 10/1998 | Hazen |
| 6,162,764 A | * | 12/2000 | Atkinson et al. ........... 504/118 |
| 6,288,009 B1 | * | 9/2001 | Kober et al. ................. 504/118 |

OTHER PUBLICATIONS

"Specification for Centrol® 3F UB, Standard Grade Lecithin (Product Code 6646)" Central Soya Company, Inc., Fort Wayne, IN, Aug. 1, 1988.

"Where Does Lecithin Come From and Lecithin for Spray Application" http://www.centralsoya.com, Sep. 6, 2001, Central Soya Company, Inc., Fort Wayne, IN.
Leciprime™, Fluid Lecithin Products Typical Composition, http://www.lecithin.com/technical/p20.html, Nov. 1, 1999.
"M–C–Thin® AF–S/UB", Lucas Meyer Inc., P.O. Box 3218, Decatur, II 62524, lecithin@midwest.net, Feb. 1999.
"Definition of Lecithin", Lucas Meyer, http://www.lucas--meyer.com/lecithin.html, Sep. 3, 1999.
"Polyacrylates", http://www.psrc.usm.edu/macrog/acrylate.htm, pp. 1–4, Sep. 3, 2001.
"Guar gum", http://www.sub.ac.uk/water/hygua.html, pp. 1–2, Sep. 3, 2001.
"Lecithins", Bernard F. Szuhaj, et al., American Oil Chemists' Society, Chapter Eight, Commerical Lecithin Products: Food Use of Soybean Lecithin, W.E. Proslse, pp. 163–167.
"Characterizing the Impact of Drift Management Adjuvants on the Dose Transfer Process", Roger A. Downer, et al., Fourth International Symposium on Adjuvants for Agrochemicals, Melbourne, Australia, Oct. 3–6, 1995, (FRI Bulletin No. 193). pp. 138–143.

(List continued on next page.)

Primary Examiner—Sabiha Qazi
(74) Attorney, Agent, or Firm—Hogan & Hartson L.L.P.

(57) ABSTRACT

Spray of discharge drift is controlled in aqueous mixtures with the inclusion of a substantially neutral pH drift control agent containing lecithin, a viscosity modifying agent, and a water dispersing agent. In one embodiment, the viscosity modifying agent is a methyl ester and the water dispersing agent is a polyoxyethylene ether. In a preferred embodiment the viscosity modify agent is methyl soyate and the water dispersing agent has the formula $H_{23}C_{11}(CH_2CH_2O)_5H$. The lecithin-based drift control agents of the present invention reduce the formation of fine droplets when the mixtures are atomized, thereby reducing the amount of the mixture that drifts outside of the area targeted to receive the spray or discharge.

18 Claims, 6 Drawing Sheets

OTHER PUBLICATIONS

"Improvement of Lecithin as an Emulsifier for Water-in-Oil Emulsions by Thermalization", John D. Weete, et al., Department of Botany and Microbiology, Auburn University, Auburn Alabama 36849, Copyright © 1994 by AOCS Press, JAOCS, vol. 71, No. 7, pp. 731–737, (Jul. 1994).

"Tomadol™ Ethoxylated Alcohols", Tomah³Products, Inc., www.tomach3.com, Jul. 9, 1999.

1998 Speciman Label L1 700® Surfactant Penetrant Acidifier, Loveland Industries, Inc., 1998.

"Soy Methyl Ester Solvents Technical Background", United Soybean Board, Weston Environmental, Analytical Chemists of Cincinnati, Feb. 2000.

Label "Tranorb™ Roundup™ Ultra Max", ©2000 Monsanto Company, St. Louis, Missouri 63167 USA.

Speciman Label "38–F® Drift Retardant", Sanag, Saritek Products, Inc., 3959 Goodwin Avenue, Los Angeles, CA 90039, Aug. 1998.

Speciman Label "41–A© Drift Retardant", Sanag™, Saritek Products, Inc., 3959 Goodwin Avenue, Los Angeles, CA 90039, Feb. 1996.

Speciman Label, Drop Zone™ DC, Database and format copyright © 1999 by C&P Press, ©copyright, Helena Chemcial Company, 1995.

Speciman Label, Strike Zone® DC, Database and format copyright © 1999 by C&P Press, ©copyright, Helena Chemical Company, 1998.

Speciman Label, "PAS–800 ™", Drexel Chemical Company, 1999.

* cited by examiner

LECITHIN-CONTAINING DRIFT REDUCTION COMPOSITION FOR USE IN SPRAYING AGRICULTURAL ACREAGE

CROSS-REFERENCE TO RELATED APPLICATION

This application claims priority of U.S. Provisional Application Ser. No. 60/377,468, filed May 1, 2002.

BACKGROUND OF THE INVENTION

1. Field of the Invention

The present invention relates to agents added to agricultural chemicals to be sprayed to crops for the purpose of reducing drift of the chemicals away from the target agricultural acreage. More particularly, the present invention relates to lecithin-containing drift reduction compositions which aid in the deposition onto and penetration into plants by aqueous sprays applied to agricultural acreage.

2. Description of the Related Art

The spraying or discharge of aqueous mixtures and solutions is important to a wide variety of agricultural crops, and involves the distribution of pesticides (including insecticides and larvaecides), herbicides, fertilizers and other agricultural products to crops and soil. However, when substantial amounts of the spray are present in the form of mist—i.e., fine droplets typically less than 141 microns in diameter—effectiveness is reduced as the mist drifts outside the area targeted for coverage. Indeed, spray droplet-size is a major factor contributing to drift. So, although smaller droplets might theoretically provide better coverage of a target area, they are more prone to drift than larger droplets.

Spray and discharge drift can prevent a substantial portion of a chemical from reaching its intended target, requiring more of the chemical to achieve adequate coverage of the target and increasing environmental pollution. For agricultural chemicals in particular, unwanted drift from the spray and discharge of herbicides and pesticides can pose a hazard to nearby crops, water supplies and livestock. Unwanted drift can also substantially increase the cost of chemical applications when necessitating repeat applications to compensate for under-treated crops.

Past research efforts to reduce spray drift have focused on improvements in the equipment used to spray or discharge aqueous mixtures on target areas. Several spray nozzle designs, for example, have been developed to optimize spray patterns and droplet size distributions. However, the most promising drift control techniques continue to be the use of additives and agents to reduce the fraction of fine droplet particles formed during the atomization of aqueous mixtures.

Experimentation has shown that the most effective drift control agents possess a number of important characteristics. Foremost, effective drift control agents significantly reduce the number of fine droplets in a spray or discharge. Effective drift control agents do not degrade or deactivate active ingredients such as pesticides, herbicides and the like. Effective drift control agents are slow to separate into a separate liquid phase on standing and during storage, and are environmentally friendly and cost efficient. Effective drift control agents need to be relatively resistant to high shear process conditions created by pumping solutions at high pressure through spray nozzles, atomizers and nebulizers.

Conventional drift control agents and additives include high molecular weight polymers that tend to increase the viscosity of an aqueous mixture or solution, hindering the atomizing mixture from breaking up into fine droplets. In the agriculture industry, for example, long chain polyacrylamides are routinely added to spray tanks as a drift reduction agents.

Unfortunately, high molecular weight, long chain polymers like polyacrylamides rapidly become less viscous when exposed to high liquid shear stresses commonly found in agricultural equipment like flow controllers, turbine metering systems, pumps, aerial spray nozzles, and so forth. The loss of polymer viscosity, called shear degradation, prevents drift control polymers from effectively suppressing fine droplet production throughout a spray application run. This is because shear degradation of drift control agents is dynamic and the polymer viscosity continually decreases the longer the drift control agents remain in a high shear stress environment. Adding additional drift control agent to compensate for the lower viscosity creates another problem—the aqueous mixture will start out too viscous at the beginning of a spray or discharge, reducing coverage efficiency.

Coverage efficiency strongly depends on the viscosity of the aqueous mixture. When viscosity gets too high coverage efficiency is reduced, requiring more solution to cover the same area as a less viscous liquid. Moreover, if the increased viscosity has resulted in a greater distribution of large-sized droplets, then the droplets have a tendency to bounce upon application. Effectiveness of foliar applications can be decreased when large droplets bounce off plant leaves and onto the ground.

U.S. Pat. No. 5,550,224 to Hazen entitled "Guar as a Drift Control Agent" discloses the use of guar and guar derivatives as drift control agents that are not affected by shear degradation. Guar is a nonionic polysaccharide that maintains its properties over a wide pH range. The guar polysaccharide is a complex carbohydrate polymer composed of essentially a straight chain of mannose units with single-membered galactose branches; chemically classified as a polygalactomannan.

In Hazen, guar compounds were added in small amounts (from 0.075% to 0.275% weight per unit volume (w/v) to aqueous mixtures, with the mixtures retaining a Newtonian fluid behavior similar to pure water. Despite having Newtonian characteristics, the aqueous guar mixtures in Hazen had significantly lower percentages of fine droplets (i.e., droplets smaller than 150 microns) than pure water. Moreover, the aqueous guar mixtures, as reported by Hazen, appeared substantially unaffected by shear forces and shear degradation, similar to pure water.

Soya lecithins, which have been reported to have drift control properties for aqueous mixtures, are surfactants used to enhance the activity and effectiveness of agricultural chemicals in aqueous mixtures. U.S. Pat. No. 4,666,747 to Quinn entitled "Spray Method and Formulation for use therein" shows aqueous aerosol sprays containing soya lecithins have a smaller percentage of droplets with diameters of 100 microns or less compared to similar sprays lacking soya lecithins. Quinn, however, does not examine how soya lecithins hold up under high shear stress.

Of course soya lecithins are widely used in agricultural. U.S. Pat. No. 3,682,653 for "Grain Conditioner-Modifier Chemical Combination" granted Aug. 8, 1972, describes a then-novel grain conditioner containing lecithin, a food grade acid and water. The preferred food grade acid is identified as propionic acid whose purpose is to reduce the lecithin pH and accomplish immediate dispersibility of the lecithin-acid chemical in water, thereby enhancing the well known and superior penetration and lubrication qualities.

One lecithin containing product presently available from Drexel Chemical Co. is PAS-800™, a mixture of phosphatidylcholine and methylacetic acid also described as containing 1.2 diacyl-SN-glycero-3-phosphorylcholine and propionic acid. It is marketed as an agricultural penetrant, acidifier and surfactant. When mixed 1% w/w with tap water, its pH has been measured as an acidic 4.02. Product label directions at recommended use rates teach application by ground or aerial equipment. Similarly, LI-700®, available from Loveland Industries, Inc., is another agricultural product identified for use as a surfactant, penetrant and acidifier. It is described as containing phosphatidylcholine, methylacetic acid and alkyl polyoxyethylene ether. When mixed 1% w/w with tap water, its pH has been measured as an acidic 3.49. There are numerous lecithin/propionic acid compositions available having a similarly acidic pH when so diluted in water.

Despite their use as a component of agricultural spray products, these acidic, lecithin-containing products do not optimally control drift. Accordingly, there remains a need for effective drift control agents for environments where shear degradation is continuously changing the ability of the drift control agent to maintain a particular mixture viscosity.

BRIEF SUMMARY OF THE INVENTION

It has now been discovered that certain substantially neutral, lecithin-containing formulations can be utilized in an aqueous mixture or solution as drift control agents with improved drift reduction resulting from optimized droplet size distribution. The lecithin-containing formulations of the present invention possess the highly desirable characteristics of efficient drift control agents and maintain these properties under prolonged high shear stress conditions that are commonly encountered during commercial spraying.

The drift control agents of the present invention contain lecithin, a methyl ester (e.g., a methylated seed oil) which functions as a viscosity modifying agent and a non-ionic surfactant which functions as a water dispersing agent. When mixed 1% w/w in tap water, the pH of the resulting composition is substantially neutral (i.e., from 6.0 to 8.0). More preferably, the pH of a 1% w/w in water is 6.5 to 7.5, with the most preferable pH range of from 6.8 to 7.2. In a preferred embodiment, lecithin constitutes from about 40% to about 60% by weight of the drift control agent, the methylated seed oil (or equivalent) constitutes from about 20% to about 30% by weight of the agent, and the non-ionic surfactant constitutes about 20% to about 30% by weight of the agent. In a more preferred embodiment of the present invention, the non-ionic surfactant comprises polyoxyethylene ether. In the most preferred embodiment, the methyl ester is methyl soyate and the non-ionic surfactant is Tomadol™, and even more preferably Tomadol™ 1-5. The most preferred formulation contains, by weight, approximately 50% lecithin, approximately 25% of the methylated seed oil and approximately 25% polyoxyethylene ether.

In other embodiments of the drift reduction agents of the present invention, 0–5% of an anti-foam agent, preferably 1–3% of the anti-foam agent, and most preferably about 2% of an anti-foam agent are also present, together with from 0–25% of a glycol, preferably 5–20% of a glycol, and most preferably 12–15% of the glycol. Diethylene glycol is a preferred glycol and SAG-47 is a preferred anti-foam agent.

DETAILED DESCRIPTION OF THE INVENTION

The drift control agent of the present invention comprises lecithin, a methyl ester and a nonionic surfactant, which when mixed 1% w/w with water, results in a solution having a substantially neutral pH (i.e., as defined herein, a pH of from 6.0 to 8.0). The preferred pH range of the 1% w/w water diluted product of the present invention is from 6.5 to 7.5, with the most preferred pH range of the 1% w/w water diluted product of from 6.8 to 7.2. The lecithin is preferably 30% to 70% by weight of the drift control agent, more preferably 40% to 60% by weight of the drift control agent, and most preferably about 50% by weight of the drift control agent. The methyl ester (most preferred being a methylated seed oil) or equivalent viscosity modifying agent is preferably 10% to 40% by weight of the drift control agent, more preferably 20% to 30% by weight of the drift control agent, and most preferably about 25% by weight of the drift control agent. The most preferred non-ionic surfactant is tomodol 1-5. The non-ionic surfactant preferably constitutes 10% to 40% by weight of the drift control agent, more preferably 20% to 30% by weight of the drift control agent, and most preferably about 25% by weight of the drift control agent.

The lecithins used in the present invention are preferably liquid, soybean based lecithins comprising mixtures of acetone insolubles, oils, and water. The acetone insolubles preferably comprise 60% to 65% by weight, more preferably about 62% by weight of the lecithin. The oils preferably comprise 34% to 40% by weight, more preferably 36% to 38% by weight of the lecithin, and water preferably comprises about 1.5% or less by weight, more preferably about 1% or less by weight of the lecithin.

The acetone insolubles in the lecithin of the present invention preferably comprise carbohydrates and polar lipids such as phospholipids and glycolipids. Preferably, the phospholipids are selected from the group consisting of phosphatidylcholines, phosphatidylethanolamines, and phosphatidylinositols. The oils preferably comprise neutral lipids such as triglycerides, and more preferably soybean oil.

Exemplary lecithins used in the present invention includes commercially available lecithins such as Centrol® 3F UB from Central Soya, Leciprime™ from Riceland Foods, Inc., and M-C-THIN® AF-S/AB from Lucas Meyer, Inc.

The methylated seed oil component of the present invention is included in the drift control agents of the present invention to make the lecithin mixture less viscous and easier to pump and stir during the spraying process. The preferred viscosity modifying agent of the present invention are methyl esters. The most preferred viscosity modifying agent is methyl soyate.

The drift control agent of the present invention includes a non-ionic surfactant to allow the drift control agent to more easily dissolve into aqueous solutions and form aqueous spray compositions. The non-ionic surfactant preferably comprises polyoxyethylene ether (an. ethoxylated alcohol) of the formula $RO(CH_2CH_2O)_nH$, where R is a linear, primary alcohol and n is the number of ethylene oxide units. The most preferable non-ionic surfactant is the polyoxyethylene ether called Tomadol™ 1-5, where R is a linear, $C_{11}$ alkyl group and n=5 to make the formula $H_{23}C_{11}O(CH_2CH_2O)_5H$.

The present invention also includes aqueous spray compositions containing the drift control agent of the present invention. These spray compositions preferably include bioactive materials such as pesticides, herbicides, fungicides, insecticides, acaricides, nematocides, foliar nutrients, defoliants, plant growth regulators, and molluscicides.

The herbicides are preferably selected from the group consisting of glyphosate (N-phosphonomethylglycine), acifluorfen (5-(2-chloro-4-(trifluoromethyl)phenoxy)-2-nitrobenzoic acid), chloramben (3-amino-2,5-dichlorobenzoic acid), 2,4-D ((2,4-dichlorophenoxy)acetic acid), endothal (7-oxabicyclo(2.2.1)heptane-2,3-dicarboxylic acid), mecoprop (2-(2-methyl-4-chlorophenoxy)propionic acid), picloram (4-amino-3,5,6-trichloropyridine-2-carboxylic acid), 2,4,5-T((2,4,5-trichlorophenoxy)acetic acid), benzac (2,3,6-trichlorobenzoic acid), dicamba (3,6-dichloro-o-anisic acid), MCPA (4-chloro-o-tolyloxyacetic acid), dalapon (2,2-dichloropropionic acid), dichlorprop (2-(2,4-dichlorophenoxy)propionic acid), MCPB (4-(4-chloro-o-tolyloxy)butyric acid), bialaphos (L-2-amino-4-((hydroxy)(methyl)phosphinoyl)butyryl-L-alanyl-L-alanine), glufosinate ((3-amino-3-carboxypropyl)methylphosphinate), imazethapyr (2-{4,5-dihydro-4-methyl-4-(1-methylethyl)-5-oxo-1H-imidazol-2-yl}-5-ethyl-3-pyridinecarboxylic acid), imazaquin (2-{4,5-dihydro-4-methyl-4-(1-methylethyl)-5-oxo-1H-imidazol-2-yl}-3-quino linecarboxylic acid), and mixtures thereof. The more preferable herbicide is an isopropylamine and/or potassium salt of glycophosate or other salts of glyphosate or glufosinate (e.g., RoundUp UltraMAX™ or Roundup WeatherMax™ from Monsanto Company or other suppliers).

The spray compositions of the present invention also preferably include one or more adjuvants selected from the group consisting of buffering agents, defoaming agents, wetting agents, sticking agents, and tank cleaners.

EXAMPLE I

A most preferred embodiment of the drift control composition of the present invention is made according to this Example I in which 50.00 grams lecithin, 25.00 grams methyl soyate and 25 grams Tomadol™ 1-5 were blended to a homogenous mixture and filtered through a 25 micron filter. When mixed 1% w/w with tap water, the pH of the resulting solution was measured at 7.08.

Figure 1:
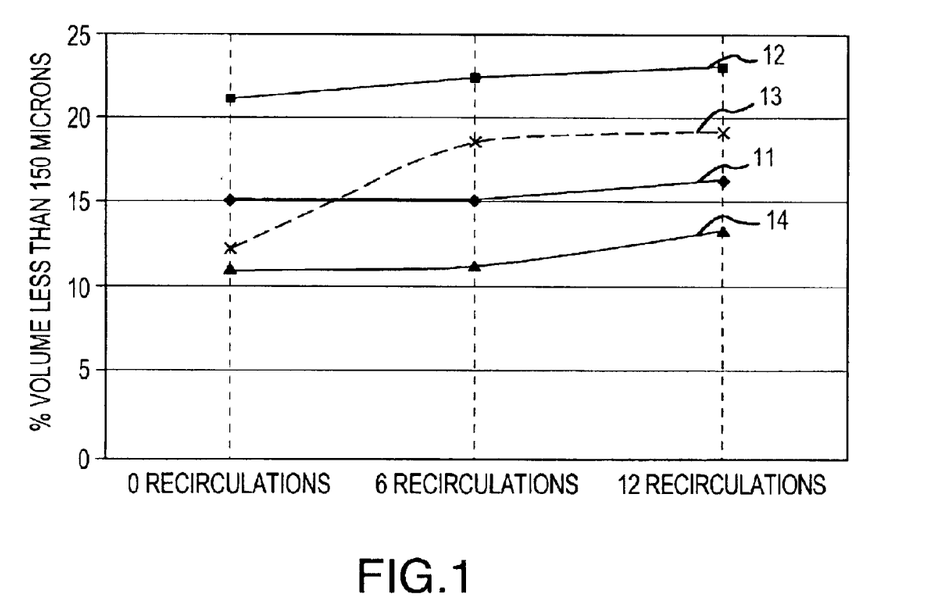
FIG. 1 is a graph illustrating the effect of pump shear on the proportion of spray volume of driftable drops for water and for a herbicide alone and combined with drift reduction agents as a function of pump cycles.

To compare the effectiveness of the drift control agents of the present invention with other known drift control agents, and to determine the efficacy of the compounds of the present invention in a high pump shear stress environment, a formulation of a most preferred embodiment of the drift control composition of the present invention was made according to Example I, and then droplet size distributions for various compounds were measured, and are shown in FIG. 1. Measurements were made for the following compositions:

(1) Water (trace 11, FIG. 1);

(2) an aqueous mixture of Roundup UltraMAX™ a glyphosate herbicide from Monsanto Company, diluted in water 2% v/v (trace 12, FIG. 1);

(3) an aqueous mixture of Roundup UltraMAX™ dilute in water 2% v/v with 41A™, a conventional polyacrylamide/polysaccharide drift reduction agent from SANAG present in the amount of 12.7 g. per 12 gallons of the mixture (formula LI-146C) (trace 13, FIG. 1); and (4) the drift control agent of the present invention from Example I in a 2% v/v UltraMAX™ glyphosate solution and 0.25% v/v Example I:glyphosate solution (formula LI-147E) (trace 14, FIG. 1).

Referring now to FIG. 1, droplet size distributions for these sprays were plotted as a function of the number of pump recirculations. The % (by vol.) of droplets <150 μm was measured at 0, 6 and 12 pump recirculations for each of the four sprays. Data displayed in FIG. 1 is summarized below in Table I.

TABLE I

| | | % by Volume of Droplets of <150 μm | | |
|---|---|---|---|---|
| | | 0 pump recirculations | 6 pump recirculations | 12 pump recirculations |
| 1 | Water | 15.09 | 15.19 | 16.12 |
| 2 | UltraMAX ™ glyphosate 2% in H₂O | 21.18 | 22.46 | 22.97 |
| 3 | UltraMAX ™ glyphosate 2% in H₂O + polyacrylamide 12.7 g/12 gal. | 12.23 | 18.44 | 19.00 |
| 4 | UltraMAX ™ glyphosate 2% in H₂O r + Example I 0.25% v/v | 10.98 | 11.13 | 13.21 |

The data in FIG. 1 show that for zero pump recirculations, the glyphosate herbicide solution spray containing no drift control agent contained about 21% by volume droplets <150 μm. Prior to pump recirculation, the percent of droplets <150 μm for glyphosate solutions and a conventional polyacrylamide drift reduction agent was measured at just over 12%. The percentage of droplets <150 μm for mixtures of the lecithin-based drift control agent of the present invention with glyphosate was measured at below 11%.

After 6 pump recirculations, a significant difference appeared between the polyacrylamide drift control agent tested and the drift control agent of the present invention. The glyphosate solution with polyacrylamide exhibited a 50% increase by volume in droplets of <150 μm, from 12% to almost 18%. In contrast, the glyphosate composition containing the drift control agent of the present invention exhibited only a slight increase by volume in droplets of <150 μm after 6 recirculations.

After 12 pump recirculations, the mixture of glyphosate and the polyacrylamide drift reduction agent exhibited a further increase by volume in droplets of <150 μm to approximately 19% by volume. The mixture of glyphosate and the drift control agent of the present invention exhibited an increase by volume in droplets of <150 μm droplets to about 13%.

Figure 2:
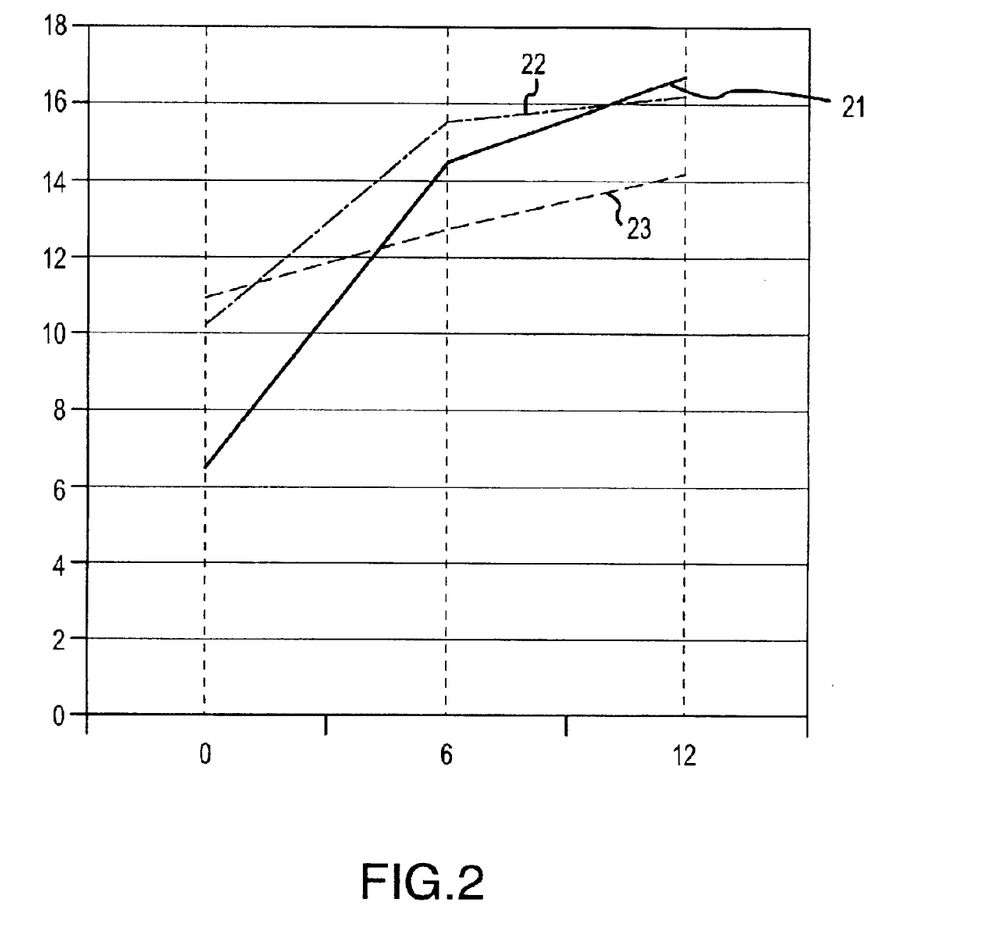
FIG. 2 is a graph illustrating the influence of pump shear on driftable fines by comparing the volume percent of fine droplet formation for herbicides combined with drift reduction agents against the number of pump cycles.

Referring now to FIG. 2, additional testing was conducted to compare droplet size distributions for sprays as a function of the number of pump recirculations for the UltraMAX™ diluted 2% v/v in water, which was added 0.25% v/v to (1) an aqueous mixture of AgRHO DR-2000® (a drift control agent based on a hydroxy propyl derivatized guar from Rhône-Poulenc Inc., (see U.S. Pat. Nos. 5,550,224 and 5,824,797 to Hazen) (trace 21), (2) a polyacrylamide (trace 22), and (3) the Example I composition (trace 23). The volume % of droplets <150 μm was measured at 0, 6 and 12 pump recirculations for each spray. Data shown in FIG. 2 is summarized in Table II.

TABLE II

| | | % by Volume of Droplets of <150 μm | | |
| --- | --- | --- | --- | --- |
| | | 0 pump recir- culations | 6 pump recir- culations | 12 pump recir- culations |
| 1 | UltraMAX ™ glyphosate 2% in water + guar DR2000 ® 1 g/l (formula LI-146J) | 6.49 | 14.93 | 16.78 |
| 2 | UltraMAX ™ glyphosate 2% in water + polyacrylamide 0.6 oz/12 gal. (formula LI-146K) | 10.17 | 15.87 | 16.23 |
| 3 | UltraMAX ™ glyphosate 2% in water + Example I 0.25% v/v (formula LI-146E) | 10.94 | 12.78 | 14.25 |

The data displayed in FIG. 2 shows that for zero pump recirculations, the glyphosate solution containing the guar drift control agent had a low percentage (just over 6%) by volume of droplets <150 μm. At zero pump recirculations, the polyacrylamide-containing formulation measured over 10% by volume of droplets <150 μm, while the glyphosate solution containing the drift control agent of the present invention also contained over 10% by volume of droplets <150 μm.

However, after 6 pump recirculations, sharp increases were measured in the volume % of small droplets for mixtures containing the standard drift control agent and the guar drift control agent. A lesser increase was measured for the spray containing the drift control agent of the present invention. The spray containing glyphosate and guar jumped from approximately 6.5% to 14.9% by volume of droplets <150 μm. The spray containing glyphosate and a polyacrylamide drift control agent climbed from 10.2% to approximately 15.9% by volume of droplets <150 μm. The spray containing glyphosate and the drift control agent of the present invention increased less steeply, from approximately 10.9% to approximately 12.8% by volume of droplets <150 μm.

After 12 pump recirculations, a slight increase was measured for the spray containing glyphosate and guar, from 14.9% to 16.8% by volume of droplets <150 μm. The spray containing glyphosate and a polyacrylamide drift control agent continued to climb from 15.9% to approximately 16.8% by volume of droplets <150 μm. The spray containing glyphosate and the drift control agent of the present invention increased from approximately 12.8% to approximately 14.25% by volume of droplets <150 μm.

The lecithin-containing drift control compositions of the present invention evidenced measurable improvement in shear resistance over other lecithin-containing compositions. Table III below compares the % of the volume of droplets of <150 μm for (a) water, (b) the UltraMAX™ glyphosate composition and (c) 3 lecithin/glyphosate compositions. The formulation of the present invention, the last line of Table III, measured the lowest percentages of the volume of droplets of <150 μm after 0, 6 and 12 pump recirculations.

TABLE III

| | | % by Volume of Droplets of <150 μm | | |
| --- | --- | --- | --- | --- |
| Formula | | 0 pump recir- culations | 6 pump recir- culations | 12 pump recir- culations |
| Water | | 15.09 | 15.19 | 16.12 |
| 2% v/v | UltraMAX ™ glyphosate | 21.18 | 22.46 | 22.97 |
| LI-146D | glyphosate/dry lecithin | 17.43 | 18.84 | 19.68 |
| LI-146A | glyphosate + LI-700 | 15.61 | 16.60 | 19.06 |
| LI-146B | glyphosate + Example I | 10.98 | 11.13 | 13.21 |

FORMULATION KEY

| Formula | Contents |
| --- | --- |
| LI-146A | 2% v/v glyphosate and 0.25% v/v LI-700 ™ in water to 12 gallons |
| LI-146B | 2% v/v glyphosate and 0.25% v/v Example I in water to 12 gallons |
| LI-146C | 2% v/v glyphosate and 12.7 g 41A ™ polyacrylamide/ polysaccharide drift reduction agent in water to 12 gallons |
| LI-146D | 2% v/v glyphosate and 25 g. dry lecithin in water to 12 gallons |
| LI-146E | 2% v/v glyphosate and 0.25% v/v Example in water to 12 gallons |
| LI-146F | 2% v/v glyphosate and 0.25% v/v (Example solution diluted 99:1 with SAG47 defoamer) in water to 12 gallons |
| LI-146G | 2% v/v glyphosate and .125% v/v Example I in water to 12 gallons |
| LI-146H | 2% v/v glyphosate and .0625% v/v Example I in water to 12 gallons |
| LI-146I | 2% v/v glyphosate and .0312% v/v Example I in water to 12 gallons |
| LI-146J | 2% v/v glyphosate and DR-2000 ™ (1 gm/L) to 12 gallons |
| LI-146K | 2% v/v glyphosate + 0.6 oz Polycontrol ™ polyacrylamide + H₂O to 12 gal |

While reducing the percentage by volume of droplets of <150 μm of an agricultural spray is expected to lead to a reduction in drift of the spray, it may not necessarily lead to greater effectiveness of the spray if there is a concomitant increase in large droplet size. This is especially true where there is a concomitant increase in large drops which reach the target, but are susceptible to bouncing off the target plants.

Figure 3:
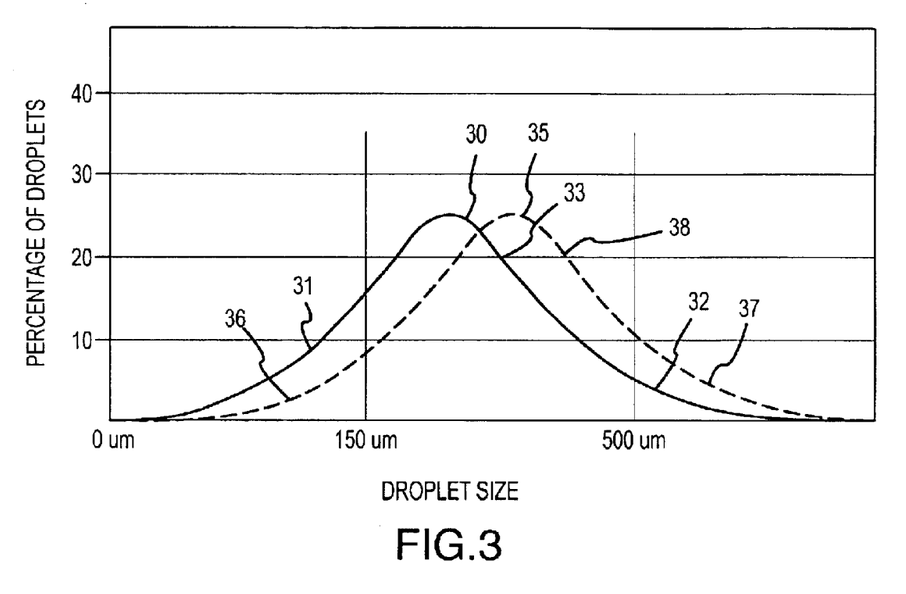
FIG. 3 is a schematic presentation of possible theoretical changes in fine droplet formation for an agricultural spray containing an agricultural chemical and a conventional drift reduction agent.

This concept is diagrammatically illustrated in FIG. 3. Shown in FIG. 3 is a "bell curve" 30 or normal distribution of droplet size of a spray to which no drift control agent has been added. The far "left" area 31 of bell curve 30 represents that portion of the spray containing drops <150 μm in size—the mist which is susceptible to drift. The far "right" area 32 of bell curve 30 represents that portion of the spray comprising large "drops" of >500 μm in size—the large drops susceptible to bounce. Central portion 33 of bell curve 30 represents the total volume of optimally-sized droplets which are expected to effectively reach the target plants. Addition of a drift control agent which merely shifts "bell curve" 30 "to the right" to form a bell curve 40, thereby creating a smaller portion 35 of drops of <150 μm but also creating an equally greater portion 36 of large drops does not increase effectiveness of the agricultural spray, as the portion 37 of bell curve 40 which are expected to effectively reach the target plants has not substantially increased over like portion 33.

Figure 4:
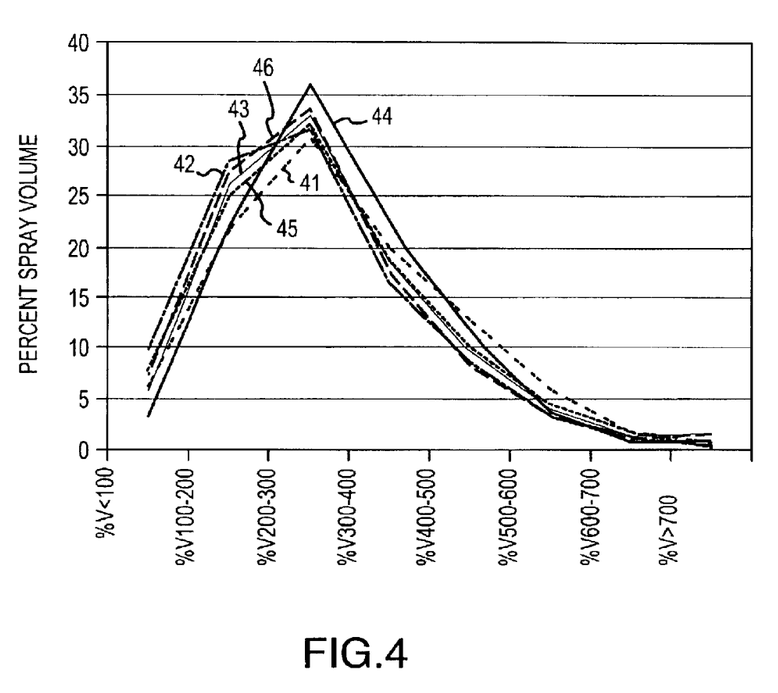
FIG. 4 is a graph showing the distribution of droplet sizes measured for aqueous compositions containing a herbicide and a lecithin-based product.

So, rather than merely minimizing the increase in fine drop percentage and concomitantly increasing the percentage by volume of large droplets susceptible to "bounce", the drift control agent of the present invention, increases the volume of mid-sized droplets expected to effectively reach the target plants. This phenomena results in an increase in the "steepness" of the bell curve—so that it more closely approximates a delta type function. Referring now to FIG. 4, it can be seen that inclusion of the drift control agent of the present invention into an aqueous solution containing 2% by volume of UltraMAX™ glyphosate, as compared to an aqueous solution containing 2% by volume of UltraMAX™ glyphosate alone and compared to an aqueous solution containing 2% by volume of UltraMAX™ glyphosate containing LI-700, a lecithin product in which the viscosity modifying agent and a water dispersing agent are not present, when measured prior to pump recirculation, results in a substantial increase in the total percentage of droplets of desired size (from ≧150 μm to ≦500 μm volume.

EXAMPLE II

In another embodiment of the present invention, 42.00 grams of crude lecithin, 21.00 grams methyl soyate, and 21 grams Tomadol™ 1-5, 14 grams diethylene glycol and 2.00 g. SAG 47™ defoamer were blended to a homogenous mixture and filtered through a 25 micron filter. A 1% w/w of the resulting solution diluted in water resulted in a measured pH of 6.80

Solutions containing this product, water, and the glyphosate compound previously discussed were mixed and tested, in the formulations described below, with the data collected as summarized below in Table IV.

TABLE IV

| Formula | Contents | % drops <150 μm | % "ideal" size | % drops >500 μm |
|---|---|---|---|---|
| Formula | Contents | 13.89 | 78.46 | 7.65 |
| LI-149B | A 2% v/v glyphosate in water to 12 gal | 20.27 | 74.61 | 5.12 |
| LI-149C | A 2% v/v glyphosate and approx. 2# ammonium sulfate in water to 12 gallons | 21.74 | 74.15 | 4.11 |
| LI-149D | A 2% v/v glyphosate, approx. 2# ammonium sulfate and approx. 12.7 g 41A ™ polyacrylamide/polysaccharide drift reduction agent in water to 12 gal | 17.72 | 75.77 | 6.51 |
| LI-149E | A 2% v/v glyphosate and approx. 4.8 oz Placement ™ biverting drift reduction agent (available from Wilber-Ellis) in water to 12 gallons | 14.75 | 80.70 | 4.55 |
| LI-149F | A 2% v/v glyphosate, approx. 2# ammonium sulfate and approx. 4.8 oz Placement ™ biverting drift reduction agent in water to 12 gallons | 15.95 | 78.44 | 5.61 |
| LI-149G | A 2% v/v glyphosate, .125% v/v Example I, and approx. 2# ammonium sulfate in water to 12 gallons | 11.00 | 84.49 | 4.51 |
| LI-149H | A 2% v/v glyphosate, .125% v/v Example II, and approx. 2# ammonium sulfate in water to 12 gallons | 12.70 | 81.90 | 5.40 |
| LI-149I | A 2% v/v glyphosate and .125% v/v Example I in water to 12 gallons | 10.16 | 84.92 | 4.92 |
| LI-149J | A 2% v/v glyphosate and .125% v/v Example II in water to 12 gallons | 10.73 | 84.35 | 4.92 |
| LI-149K | A 2% v/v glyphosate and approx. 1.08# Array ™ an ammonium compound with defoamer with water to 12 gallons | 10.52 | 64.90 | 24.58 |
| LI-149L | A 2% v/v glyphosate, approx. 1.08# Array ™ an ammonium compound with defoamer, and approximately 14.4 oz Borosol ™ available from Loveland Industries, with water to 12 gallons | 10.59 | 65.76 | 23.65 |
| LI-149M | A 2% v/v glyphosate, .125% v/v Example II, and approximately 14.4 oz Borosol ™, with water to 12 gallons | 11.73 | 83.25 | 5.02 |
| LI-149N | A 2% v/v glyphosate, 125% v/v Example II, and 0.5% v/v Choice ™ water conditioning agent from Loveland Industries, to 12 gallons | 14.33 | 81.56 | 4.11 |

It can thus be appreciated that essentially the drift control agents of the present invention create a better droplet size spectrum by reducing the percentage of fine droplets (<150 μm) released by a spray or discharge apparatus. By reducing the proportion of fine droplets of a spray of an aqueous mixture, more of the mixture falls over the target acreage. In addition, however, the drift control agents of the present invention do not concomitantly increase the percentage of very large droplets. This is important because excessively large droplets tend to "bounce" off of leaves and other vegetation. When such large droplets successfully reach target acreage, they are not retained by and do not act upon the target vegetation as desired.

Selective date from Table IV is rounded and summarized in Table V for further clarity:

TABLE V

| | % Driftable | % ideal Size | % Too Large |
|---|---|---|---|
| Roundup UltraMax 2% v/v | 20.3% | 74.6% | 5.1% |
| Polyacrylamide 41A (0.28 g/l) and UltraMax 2% v/v | 17.7% | 75.8% | 6.5% |
| Lecithin-based Example II solution 0.125% v/v and UltraMax 2% v/v | 12.7% | 81.9% | 5.4% |
| Starch base Array at 9 lb/100 gal and UltraMax 2% v/v | 10.5% | 64.9% | 25.0% |

Referring to TABLE V, it can been seen that while the starch-based product has the smallest percentage of driftable drops at 10.5%, it also has the largest percentage of excessively large drops at 25.0%, resulting in the smallest percentage (at 64.9%) of ideal size drops. In comparison, it can be seen that the lecithin-based Example II solution has, at 81.9%, the largest percentage of ideal size drops.

Figure 5:
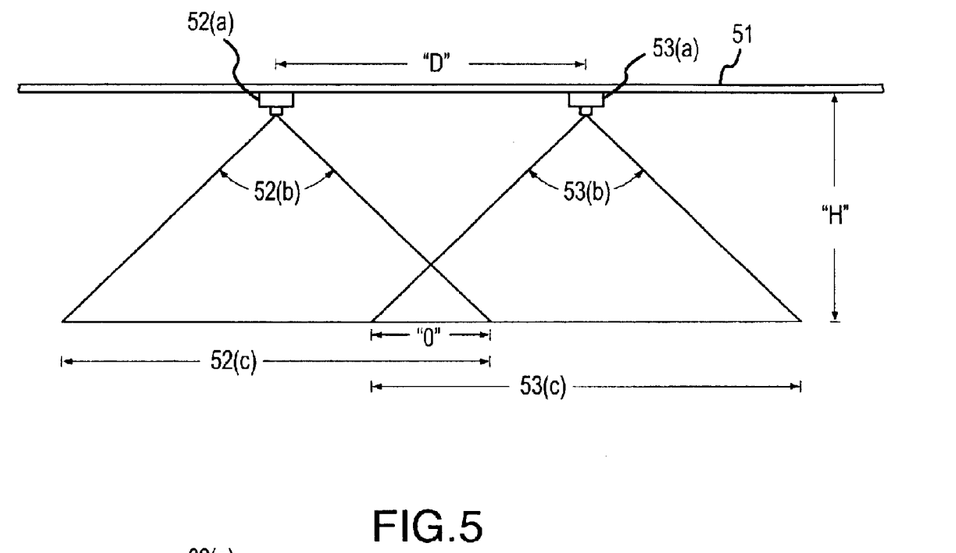
FIG. 5 is a diagrammatic representation of preferred spray patterns of adjacent nozzles of an agricultural spray system.

By creating and maintaining an optimized drop size spectrum, the drift control agents of the present invention are able to maintain proper nozzle performance in agricultural spray systems. As diagrammatically illustrated in FIG. 5, a boom 51 delivers agricultural solutions to first nozzle 52(*a*) and second nozzle 53(*a*) a distance "D" apart. Nozzles 52(*a*) and 53(*a*) each are designed to deliver a spray pattern of equal fan angles 52(*b*) and 53(*b*), respectively, resulting in spray coverage of diameters 52(*c*) and 53(*c*), respectfully, with a desired overlap area "O" when boom 51 is positioned at a predetermined boom height "H". When the viscosity of the agricultural solution to be sprayed and optimized droplet size spectrum are maintained, the desired overlap area "O" is maintained.

Figure 6:
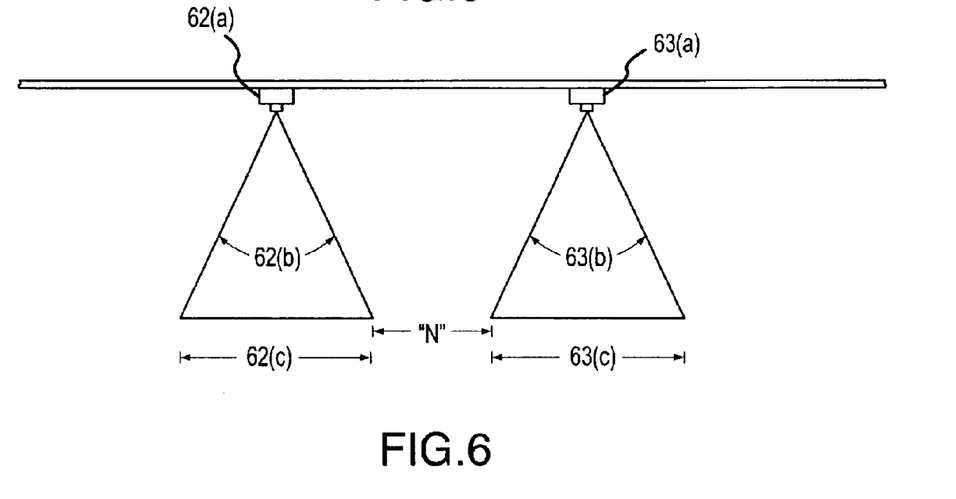
FIG. 6 is a diagrammatic representation of pinched down spray patterns of adjacent nozzles in an agricultural spray system.

On the other hand as viscosity of agricultural spray solutions increase, as illustrated diagrammatically in FIG. 6, nozzles 62(*a*) and 63(*a*) actually deliver spray patterns having pinched down spray fan angles 62(*b*) and 63(*b*), respectively, resulting in spray coverage of diameters 62(*c*) and 63(*c*), respectively, which have a compromised overlap. The comprised overlap may be either smaller that the overlap area for which the system was originally engineer or may even result in an area "N" having no spray coverage, an obviously undesirable result.

Figure 7:
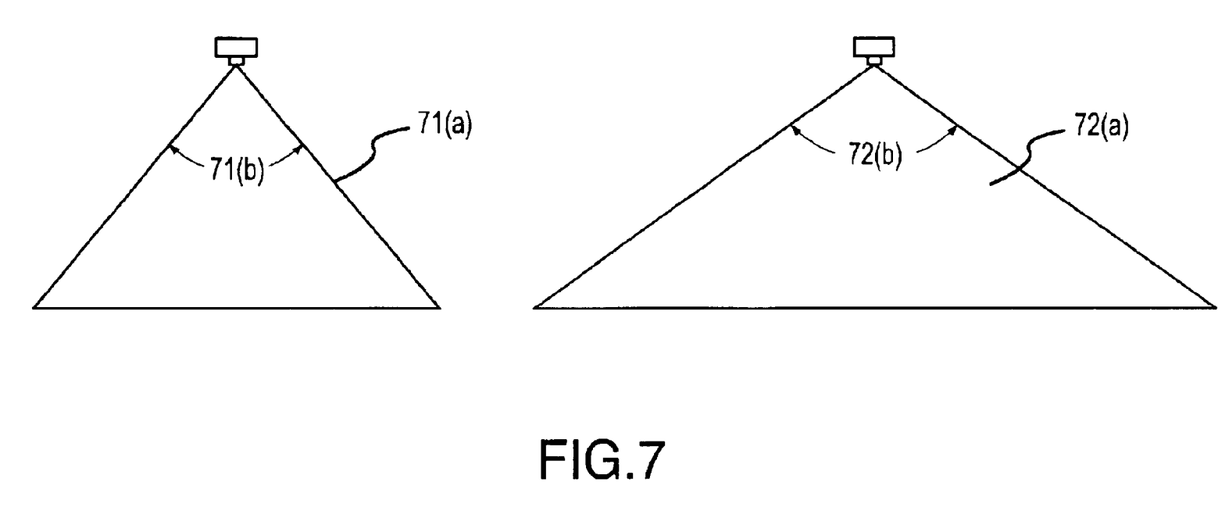
FIG. 7 is an illustration comparing a preferred nozzle spray pattern with a pinched down nozzle spray pattern.

FIG. 7 illustrates a comparison of two spray patterns. Spray pattern 71(*a*) illustrates the spray silhouette of a solution of Roundup® UltraMax 2% v/v to which is added a polyacrylamide drift reduction agent at a standard application rate of 9 pounds per 100 gallons of solution at field application rates. Spray pattern 71(*a*) has an approximate fan or distribution angle 71(*b*) of 80°. In contrast, spray pattern 72(*a*) illustrates the spray silhouette of a solution of Roundup® UltraMax 2% v/v to which is added a 0.25% v/v Example I solution. Spray pattern 72(*a*) has an approximate fan or distribution angle 72(*b*) of 110°. Only the latter spray angle will result in the needed overlap area between adjacent nozzles at a conventional boom height under generally expected operating conditions.

When applying spray to agricultural crops, it is not only important to maintain a spray distribution angle for which a particular nozzle is designed, it is also important to achieve an even spray distribution throughout the spray coverage area. When spray is not evenly distributed, hot spots (areas of excessive coverage) and weak spots (areas of no or insufficient coverage) are created. An even spray distribution is indicated by a low (approaching 0) coefficient of variation (CV). An increased incidence of hot and weak spots is evidenced by a greater coefficient of variation.

Spray patterns were measured for coefficients of variation for water and six formulations at 16–17 inches from the nozzle and 23–24 inches from the nozzle. Each of the six formulations were standardized so as to also include 2% by weight of ammonium sulfate. The results of these measurements are summarized below in Table VI.

TABLE VI

|  | % CV 16"–17" from nozzle | % CV 23"–24" from nozzle |
|---|---|---|
| Water | 11 | 6 |
| WeatherMax ™ glyphosate 1.3 wt % | 7 | 13 |
| WeatherMax ™ glyphosate 1.3 wt % + 9 lb/100 gal Thrust ™ polyacrylamide | 9 | 8 |
| WeatherMax ™ glyphosate 1.3 wt % + 9 lb/100 gal Array ™ starch base product | 21 | 58 |
| WeatherMax ™ glyphosate 1.3 wt % + 9 lb/100 gal Spray-Start polyacrylamide | 13 | 13 |
| WeatherMax ™ glyphosate 1.3 wt % + 0.25% Example I solution | 4 | 9 |
| WeatherMax ™ glyphosate 1.3 wt % + 0.125 Example II solution | 6 | 9 |

The most noteworthy result was the extreme increase in variable spray measured with the Array™ starch-based product, where the % CV increased from 13 for a glyphosate/ammonium sulfate solution alone to 58 when Array™ was added to the mixture, measured at 23–24 inches from the nozzle. In contrast, addition of the Example I and Example II solutions (in the alternative) resulted both cases in a decrease in % CV from 13 to 9.

The drift control agents of the present invention may alternatively be applied to solid products such as ammonium sulfate, and the treated product then transported to the fields on which the product is to be used. In the field, the treated product is then dissolved in a tank mix, and the final mixture sprayed with drift effectively reduced. In a preferred formulation, a precipitated silica is added to ammonium sulfate and mixed well. While mixing continues, the Example II drift reduction composition is added. The preferred formulation is 85.00 wt % ammonium sulfate, 4.65 wt % precipitated silica, and 10.36% Example II solution. The measured pH of this mixture diluted in tap water to form a 1% (wt %) solution is approximately 6.6.

When mixtures containing the drift control agents of the present invention are sprayed or discharged from high altitudes, they are not only less prone to atomize into fine droplet mists that will blow and drift outside the target area, the presence of the surfactant lecithin with its surface-tension reducing qualities has other benefits. The presence of lecithin makes it more likely that the spray compound will cling to the tops of vegetation and be absorbed where it lands, instead of beading up and rolling onto the ground.

The drift control agents of the present invention exhibit rapid dispersion and hydration in water and biodegradable. Separation of the drift control agent of the present invention into a separate liquid phase in the aqueous mixture upon standing or storage is minimized. Clogging of spray nozzles and compound freezing are minimized with the drift control agent of the present invention. These agents are also ion insensitive and can remain effective when admixed with hard or brackish water.

We claim:

1. A drift control agent comprising:
   lecithin;
   a methyl ester; and
   a non-ionic surfactant, wherein when said drift control agent is diluted 1% w/w in water, the pH of the resultant composition is from 6.0 to 8.0.

2. The drift control agent of claim 1, wherein said methyl ester is a methylated seed oil.

3. The drift control agent of claim 1, wherein said methyl ester is methyl soyate.

4. The drift control agent of claim 1, wherein said non-ionic surfactant comprises a polyoxyethylene ether having the formula $RO(CH_2CH_2O)_nH$.

5. The drift control agent of claim 1, wherein said polyoxyethylene ether is a compound having the formula $H_{23}C_{11}O(CH_2CH_2O)_5H$.

6. A drift control agent comprising:
   40%–60% w/v lecithin;
   20%–30% w/v methyl ester; and
   20%–30% w/v non-ionic surfactant, wherein when said drift control agent is diluted 1% w/w in water, the pH of the resultant solution is from 6.0 to 8.0.

7. The drift control agent of claim 6, wherein said methyl ester is a methylated seed oil.

8. The drift control agent of claim 6, wherein said methyl ester is methyl soyate.

9. The drift control agent of claim 6, wherein said non-ionic surfactant comprises a polyoxyethylene ether having the formula $RO(CH_2CH_2O)_nH$.

10. The drift control agent of claim 9, wherein said polyoxyethylene ether is a compound having the formula $H_{23}C_{11}O(CH_2CH_2O)_5H$.

11. A method for reducing the drift during release of an aqueous composition comprising the step of:
- forming an agricultural composition suitable for treating agricultural acreage by mixing water, a bioactive material and a drift control agent comprising lecithin, a methyl ester, and a non-ionic surfactant; and
- spraying the agricultural composition on agricultural acreage. wherein when said drift control agent is diluted 1% w/w in water, the pH of the resultant composition is from 6.0 to 8.0.

12. The method of claim 11, wherein the bioactive material is selected from the group consisting of pesticides, herbicides, fungicides, insecticides, acaricides, nematocides, foliar nutrients, defoliants, plant growth regulators, and molluscicides.

13. The method of claim 12, wherein the drift control agent contains 40%–60% by weight lecithin, the methyl ester constitutes 20%–30% by weight of the drift control agent, and the non-ionic surfactant is a polyoxyethylene ether which constitutes 20%–30% by weight of the drift control agent.

14. The method of claim 13, wherein the drift control agent is present in the agricultural composition from 0.0312% to 2% weight per unit volume.

15. The method of claim 13, wherein the drift control agent is present in the agricultural composition from 0.125% to 1% weight per unit volume.

16. The method of claim 13, wherein the drift control agent is present in the agricultural composition from 0.25% to 2% weight per unit volume.

17. The method of claim 13, wherein the mixing step further includes adding a one or more adjuvants selected from the group consisting of buffering agents, defoaming agents, wetting agents, sticking agents, and tank cleaners.

18. The method of claim 11, wherein in the bioactive material is a herbicide selected from the group consisting of glyphosate and N-(phosphonomethyl)glycine.

* * * * *